United States Patent [19]

Straub

[11] Patent Number: 4,698,221

[45] Date of Patent: Oct. 6, 1987

[54] VACCINES CONTAINING FAT SOLUBLE VITAMINS, ZINC COMPOUNDS AND SELENIUM COMPOUNDS

[75] Inventor: Otto C. Straub, Tübingen, Fed. Rep. of Germany

[73] Assignee: Bayer Aktiengesellschaft, Leverkusen, Fed. Rep. of Germany

[21] Appl. No.: 585,680

[22] Filed: Mar. 2, 1984

Related U.S. Application Data

[63] Continuation-in-part of Ser. No. 547,829, Nov. 2, 1983, abandoned.

[30] Foreign Application Priority Data

Nov. 6, 1982 [DE] Fed. Rep. of Germany ....... 3241113

[51] Int. Cl.$^4$ ..................... A61K 39/12; A61K 39/00; A61K 39/02
[52] U.S. Cl. ........................................ 424/89; 424/88; 424/92
[58] Field of Search ....................... 424/88, 89, 91, 92; 426/73, 656; 514/168, 458, 904

[56] References Cited

U.S. PATENT DOCUMENTS

| | | | |
|---|---|---|---|
| 2,980,588 | 4/1961 | Larde | 514/904 X |
| 3,531,565 | 9/1970 | Webb et al. | 424/88 X |
| 3,551,554 | 12/1970 | Herschler | 424/89 X |
| 3,594,471 | 7/1971 | Hertzberger | 424/88 X |
| 4,073,743 | 2/1978 | Midler, Jr. et al. | 252/309 |
| 4,075,333 | 2/1978 | Josse | 514/904 X |
| 4,298,601 | 11/1981 | Howard | 426/657 X |

FOREIGN PATENT DOCUMENTS

| | | |
|---|---|---|
| 888180 | 1/1962 | United Kingdom . |
| 983490 | 2/1965 | United Kingdom .......... 424/88 |
| 1163470 | 9/1969 | United Kingdom . |
| 1171783 | 11/1969 | United Kingdom .......... 424/88 |
| 1189340 | 4/1970 | United Kingdom . |
| 2030043 | 4/1980 | United Kingdom .......... 424/92 |

OTHER PUBLICATIONS

Chem. Abs. 91:151391h (1979).
Chem. Abs. 86:65606x (1977).
Chem. Abs. 78:24162r (1973).
Chem. Abs. 83:94772s (1975).
Chem. Abs. 99:93719y (1983).
Bulletin de l'Institut Pasteur, vol. 75(1): 27–29, 56–60, Jan. 1977.
Chem. Abs. 101:208772q (1984).
Siedemann et al., Nutrit. Rep. International, 21(6): 931–942 (1980).

*Primary Examiner*—Sam Rosen
*Assistant Examiner*—Shawn P. Foley
*Attorney, Agent, or Firm*—Sprung Horn Kramer & Woods

[57] ABSTRACT

The invention relates to vaccines which, in addition to antigens, contain fat-soluble vitamins (such as vitamins A, D or E), physiologically acceptable zinc and selenium compounds and, optionally, absorption-promoting agents and/or spreading oils.

20 Claims, No Drawings

VACCINES CONTAINING FAT SOLUBLE VITAMINS, ZINC COMPOUNDS AND SELENIUM COMPOUNDS

This is a continuation-in-part application of Ser. No. 547,829 filed Nov. 2, 1983 (now abandoned).

The invention relates to vaccines which, in addition to antigens, contain fat-soluble vitamins, physiologically acceptable zinc and selenium compounds, and, optionally, absorption-promoting agents and/or spreading oils.

It has been found that vaccines containing antigens and (a) fat-soluble vitamins, physiologically acceptable zinc and selenium compounds and, optionally, (b) an absorption-promoting agent and/or (c) a spreading oil, have substantial advantages in respect of cell-mediated immunity compared with vaccines known from the prior art.

The vaccines according to the invention particularly preferably contain the anthelmintic compounds tetramisole or levamisole that is to say ($\pm$)-2,3,5,6-tetrahydro-6-phenylimidazo-[2,1-b]thiazole or its levorotatary form, in amounts of 50–1,000 mg, preferably 100–300 mg.

Vitamins A, D and/or E are preferably used as the fat-soluble vitamins in the vaccines according to the invention.

The vaccines according to the invention preferably contain, as antigens, IBR/IPV viruses, PI-3 viruses, BVD viruses, adenoviruses, reoviruses, RSV viruses or rotaviruses, and bacteria, such as Pastorella, Multocita and Corynebacteria, in activated or non-activated form.

The vaccines according to the invention have proved particularly advantageous for combating and prophylaxis of virus diseases when they contain the following amounts of the abovementioned additives: (a) 20,000 to 600,000 units, preferably 50,000 to 500,000 units and most preferably 80,000 to 160,000 units of the fat-soluble vitamins A; 20,000 to 600,000 units, preferably 20,000 to 100,000 units and most preferably 40,000 to 80,000 units of the fat-soluble vitamin D; 100 to 1000 mg., preferably 500 to 800 mg of vitamin E; 100 to 1,000 mg., preferably 50 to 500 mg and most preferably 50 to 200 mg of physiologically acceptable selenium compounds; and 10 to 2,000 mg., preferably 50 to 200 mg. and most preferably 50 to 150 mg of physiologically acceptable zinc compounds, (b) 20 to 95 parts by weight, preferably 60 to 90 parts by weight more preferably 5 to 40 parts by weight and most preferably 10 to 20 parts by weight of an absorption-promoting agent and, (c) 0.5 to 50 parts by weight, preferably 1 to 20 parts by weight and more preferably 1 to 5 parts by weight of the spreading oil.

Preferably, 60,000 to 600,000 units of vitamin A and 20,000 to 200,000 units of vitamin $D_3$ are employed.

The vaccines according to the invention can contain bovine thymus extract as a further aditive for improving cell-mediated immunity. For this purpose, bovine thymus (for example 1 part by weight of thymus tissue per part by weight of PBS) is homogenized, deep-frozen, thawed and centrifuged and the supernatant is used as the additive.

Physiologically active amounts of the antiprostaglandins (see, for example, XIIth World Congress on Diseases of Cattle, The Netherlands, World Association for Biuatrics, Procedings Volume I, Sept. 7–10, 1982) can also be added to the vaccines.

Particularly suitable absorption-promoting agents which can be used for the preparation of the vaccines according to the invention are:

Alkanols, such as ethyl alcohol, isopropyl alcohol, n-butyl alcohol and amyl alcohol.

Glycols, such as ethyleneglycol, propyleneglycol and 1,3-butyleneglycol. Aromatic alcohols, such as benzyl alcohol. Trihydric alcohols, particularly trihydric alkanols having 3 to 6 carbon atoms, such as glycerol.

Carboxylic acid esters, such as, for example, ethyl acetate, benzyl benzoate and butyl acetate.

Aromatic and/or aliphatic hydrocarbons.

Oils which do not fall within the definition of spreading oils: such as, for example, cotton seed oil, ground nut oil, maize germ oil, olive oil, castor oil and sesame oil.

Water

Ketones, such as, for example, acetone and methyl ethyl ketone.

Compounds such as dimethylsulphoxide, dimethyl acetamide, dimethylformamide, N-methylpyrrolidone, dioxane and 2-dimethyl-4-oxymethyl-1,3-dioxalane, inter alia, have also proved particularly suitable.

Lower alcohols with up to 7 carbon atoms in the molecule, as well as lower ketones, such as, for example acetone and methyl ethyl ketone, and lower halogented hydrocarbons, especially lower halo-alkanes, such as, for example, methylene chloride, are especially suitable.

One or more absorption-promoting agents can be used in the preparation of the vaccines according to the invention.

In principle, all the organic and inorganic solvents which take up the antigens in a sufficient concentration and permit adequate absorption of the vaccines through the skin without damage to the tissue are possible as absorption-promoting agents suitable for the preparation of the vaccines according to the invention.

Virtually all the substances which have the properties already mentioned above are suitable as spreading oils. In particular, the following classes of compound and compounds are suitable:

silicone oils of various viscosities, fatty acid esters, such as ethyl stearate, di-n-butyl adipate, hexyl laurate, dipropylene glycol pelargonate, esters of a branched fatty acid of medium chain length and saturated $C_6$–$C_{18}$ fatty alcohols, isopropylmyristate, isopropylpalmitate, caprylates and caprates of saturated fatty alcohols of $C_{12}$–$C_{18}$ chain length, isopropyl stearate, oleyloleate, decyloleate, ethyloleate, ethyllactate, waxy fatty acid esters, such as synthetic duck uropygial gland oil, dibutylphthalate, diisopropyladipate, ester mixtures related to the latter and the like.

Triglycerides, such as caprylic/capric acid triglyceride, triglyceride mixtures with plant fatty acids of $C_8$–$C_{12}$ chain length or other specifically selected natural fatty acids, partial glyceride mixtures of saturated or unsaturated fatty acids, which may also contain hydroxyl groups, monodiglycerides of the $C_8$–$C_{10}$-fatty acids and others.

Fatty alcohols, such as isotridecyl alcohol, 2-octyldodecanol, cetylstearyl alcohol and oleyl alcohol.

Fatty acids, such as, for example oleic acid.

Spreading oils which are particularly suitable are the following: isopropylmyristate, isopropylpalmitate, caprylates/caprates of saturated fatty alcohols of $C_{12}$–$C_{18}$ chain length and waxy fatty acid esters, such as synthetic duck uropygial gland oil.

Zinc and selenium compounds which are suitable additives are:

zinc aspartate, zinc lactate, zinc halides, such as zinc iodide and zinc fluoride, zinc sulphate, zinc myristate, the zinc disodium salt of ethylenediaminetetraacetic acid, zinc phosphates, zinc tartrates and zinc citrates, in physiologically acceptable amounts.

Selenium halides, such as selenium chloride and selenium fluoride;

Selenides, such as $Na_2Se$; selenium oxide; selenious acid, selenites and the like, in physiologically acceptable amounts.

The vaccines are administered parenterally by inoculation or applied locally by spraying (for example for combating IBR/IPV in the respiratory, digestive or genital tract of cattle).

To prepare the vaccines, the antigens and the additives are mixed and the mixture is homogenised. The pH value is adjusted to 5 to 8, but preferably to the neutral value, by means of suitable buffers. Water and other pharmacologically acceptable solvents are used as carriers for the vaccines according to the invention.

The dose in which the vaccines according to the invention are used is as a rule 2 to 10 ml per animal.

A vaccine dose of 6 ml, for example, contains: 2 ml antigens, 0.2 ml zinc compound, 0.2 ml sodium selenite, 0.6 ml dimethylsulfoxide, 0.5 ml spreading oil, 0.5 ml vitamin E, 0.5 ml vitamin A, 0.5 ml vitamin D and 1 ml levamisole.

EXPERIMENTAL REPORT 1/CATTLE 2 groups of cattle (19 animals/25 animals) were inoculated subcutaneously with inactivated IBR/IPV virus suspension (inactivated with ethyleneimine), which in one case contained the additives according to the invention (19 animals) and in the other case contained no additives (25 animals). After 6 weeks, the inoculation was repeated, and after 9 months the titer was determined in a serum neutralisation test. The animals which had been inoculated with the additives according to the invention had an average titer of 1:10.4. Without the additives, the titer was 1:6.

The pH value of the inoculum was 5.2. A dose of 2.5 ml was used.

Additives 0.5 ml of commercially available vitamin A, D and E preparation corresponding to 150,000 units of A, 100,000 units of D and 150 mg of E, 0.5 ml of 10% strength levamisole solution; 0.25 ml of Zn salt solution corresponding to 50 mg of Zn, 0.25 ml of Na selenite solution corresponding to 100 mg of Se; and 1.25 g of medium (water).

No irritations of the skin or increases in temperature were to be observed after administration of this vaccine.

EXPERIMENTAL REPORT 2/SHEEP

A vaccination experiment was carried out on sheep. For this, the animals were inoculated with an inactivated IBR/IPV vaccine (inactivated with ethyleneamine). (a) without additives and (b) with the additives according to Experimental report 1, at an interval of 2 months.

The pH value of the inoculum with additives was 5.2.

The serum neutralisation test gave the following titers in $-\log 10$.

| 2 months after the first inoculation | with | (a) | 0.45 |
|---|---|---|---|
| | and | | 0.00 |
| | with | (b) | 1.05 |
| | and | | 0.90 |
| 1 month after the second inoculation | with | (a) | 1.20 |
| | and | | 0.75 |
| | with | (b) | 1.95 |
| | and | | 1.35 |

Accordingly, the additives effect a considerable improvement in the immunogenic action of the vaccines.

What is claimed is:

1. A vaccine composition containing an immunologically effective amount of an antigen, an immunologically effective amount of at least one fat soluble vitamin and immunologically effective amounts of at least one physiologically acceptable zinc compound and at least one physiologically acceptable selenium compound.

2. A vaccine composition of claim 1 further comprising (a) an absorption promoting agent and/or (b) a spreading oil.

3. A vaccine composition of claim 2 further comprising at least one absorption-promoting agent in combination with levamisole and/or an antiprostglandin.

4. A vaccine composition of claim 3 further comprising a spreading oil.

5. A vaccine composition according to claim 1 which further comprises levamisol and/or an antiprostaglandin.

6. A vaccine composition according to claim 1, wherein the fat soluble vitamin is vitamin A, D and/or E.

7. A vaccine composition according to claim 1, containing (a) 20,000 to 600,000 units of each of the fat soluble vitamins A and D, 100 to 1,000 mg of vitamin E, 100 to 1,000 mg of physiologically acceptable selenium compounds, 50 to 1,000 mg of physiologically acceptable zinc compounds and 20 to 95 parts by weight of an absorption-promoting agent.

8. A vaccine composition according to claim 7, further comprising 50 to 1,000 mg levamisole.

9. A vaccine composition according to claim 7 wherein the absorption-promoting agent is a compound selected from the group consisting of alkanols, glycols, aromatic alcohols, trihydric alcohols, carboxylic acid esters, aromatic and aliphatic hydrocarbons, non-spreading oils, water and ketones.

10. A vaccine composition according to claim 1 which further comprises dimethylsulphoxide or isopropyl alcohol.

11. A vaccine composition of claim 10, further comprising isopropylmyristate as a spreading oil.

12. A vaccine composition according to claim 1 wherein the antigen is selected from the group consisting of IBR/IPV viruses, PI-3 viruses, BBT viruses, adenoviruses, reoviruses, RSV viruses, retroviruses, coroviruses, poxviruses or rotaviruses and bacteria, in activated or inactivated form.

13. A vaccine composition according to claim 12 wherein the bacteria are Pastorella, Multocita or Corynebacteria.

14. A vaccine composition according to claim 1 wherein the zinc compound is selected from the group consisting of zinc aspartate, zinc lactate, zinc iodide, zinc fluoride, zinc sulphate, zinc myristate, the zinc disodium salt of ethylenediamine tetraacetic acid, zinc phosphate, zinc tartrate and zinc citrate.

15. A vaccine composition according to claim 1 wherein the selenium compound is selected from the group consisting of sodium selenite and potassium selenite.

16. A vaccine composition according to claim 1 further comprising a spreading oil selected from the group consisting of isopropyl myristate, isopropyl palmitate, a caprylate, a caprate of a saturated fatty acid of $C_{12}$–$C_{18}$-chain length and a waxy fatty acid ester.

17. A vaccine composition according to claim 16 wherein the waxy fatty acid ester is synthetic duck uropygial gland oil.

18. A vaccine composition according to claim 1 further comprising an absorption promoting agent selected from the group consisting of dimethylsulphoxide, dimethylacetamide, dimethylformamide, N-methylpyrrolidone, dioxane and 2-dimethyl-4-oxomethyl-1,3-dioxalene, a lower alcohol with up to 7 carbon atoms in the molecule, a lower ketone and a lower halogenated hydrocarbon.

19. A method of preparing a vaccine composition which comprises adding to an antigen, fat soluble vitamins and physiologically acceptable selenium and zinc compounds all in effective amounts.

20. A method according to claim 19 wherein dimethylsulphoxide is added as an absorption-promoting agent.

* * * * *